United States Patent [19]

Gerson et al.

[11] Patent Number: 5,300,422

[45] Date of Patent: Apr. 5, 1994

[54] SCREENING METHOD FOR CONTROLLING AGRANULOCYTOSIS

[75] Inventors: Stanton L. Gerson, Pepper Pike; Herbert Meltzer, Shaker Heights, both of Ohio

[73] Assignee: Case Western Reserve University, Cleveland, Ohio

[21] Appl. No.: 802,162

[22] Filed: Dec. 4, 1991

[51] Int. Cl.$^5$ .................... C12Q 1/00; G01N 33/48
[52] U.S. Cl. .......................... 435/4; 436/63; 436/74; 436/815; 424/9; 514/255
[58] Field of Search ............... 435/4; 436/63, 74, 815; 424/9; 514/255

[56] References Cited

U.S. PATENT DOCUMENTS 5,013,735 5/1991 Björk ................................ 514/255

OTHER PUBLICATIONS

Koue et al, *Arch. Gen. Psychiatry*, vol. 45, No. 9, pp. 789–796, Sep. 1988.
Baldessarini et al, *The New England Journal of Medicine*, vol. 324, No. 11, pp. 746–754, Mar. 4, 1991.
Gerson et al, *The Lancet*, vol. 340, p. 1097, Oct. 31, 1992.
Pisciotta et al, *J. Lab., Clin. Med.*, vol. 119, No. 3, pp. 254–266, Mar. 1992.
Terkelsen et al, *Hosp. Community Psychiatry*, vol. 41, No. 8, pp. 863–869, Aug. 1990.
Claas *Psychopharamacology*, vol. 99/Suppl., pp. 113–117, 1989.
Bastani et al, *Psychopharmacology*, vol. 99/Suppl., pp. 122–125, 1989.

*Primary Examiner*—Michael G. Wityshyn
*Assistant Examiner*—Abdel A. Mohamed
*Attorney, Agent, or Firm*—Robert S. Honor; Melvyn M. Kassenoff; Joseph J. Borovian

[57] ABSTRACT

A screening method for detecting the vulnerability of patients on clozapine therapy to developing agranulocytosis which comprises establishing the concentration of N-desmethylclozapine in the blood or bone marrow of said patient. In addition, a method of determining patient sensitivity to N-desmethylclozapine is provided which comprises collecting heparinized blood and assaying it for stem cell sensitivity to N-desmethylclozapine.

14 Claims, No Drawings

SCREENING METHOD FOR CONTROLLING AGRANULOCYTOSIS

This invention relates to a method of screening patients undergoing drug therapy for vulnerability to drug-induced agranulocytosis. More particularly, it relates to a screening method for detecting the vulnerability of patients on clozapine therapy to developing agranulocytosis which comprises establishing the concentration of N-desmethylclozapine in the blood or bone marrow of said patients.

BACKGROUND OF THE INVENTION

Agranulocytosis is an infrequent but potentially fatal complication associated with certain drugs that otherwise have less serious side effects and ordinarily are harmless to most patients. The complication is characterized by leukopenia (white blood count less than 2000/cu.mm.), a total absence of polymorphonuclear leukocytes (defined as less than 500/cu.mm.) and relative lymphopenia. If the disorder goes unrecognized and treatment with the drug is not discontinued, agranulocytosis will run a progressive course of increasing severity culminating in death from infection. If treatment with the drug is discontinued, complete recovery usually occurs. The period of greatest risk of agranulocytosis developing is in the first 3 to 12 weeks of treatment.

Antipsychotic drugs such as neuroleptics, tricyclic antidepressants and the benzodiazepines have been implicated in producing agranulocytosis. The most significant of these is the atypical neuroleptic drug, clozapine, whose chemical name is 8-chloro-11-(4-methyl-1-piperazinyl)-5H-dibenzo[b,e]-[1,4]diazepine. Clinical studies have shown that clozapine is effective as an antipsychotic agent in patients who are refractory and/or intolerant to classical antipsychotic drug treatment. The compound was found to be superior to standard neuroleptics; and approximately 30% of the patients conservatively defined as being refractory to these neuroleptics significantly improved with clozapine treatment. At the same time, it was found that clozapine does not cause parkinsonism or tardive dyskinesia to the same extent as classical neuroleptics and that it does not elevate prolactin secretion. With regard to tardive dyskinesia, long term treatment with clozapine appears to have a therapeutic effect against this neuroleptic side-effect, particularly the more severe form, tardive dystonia.

Despite its advantages, development of clozapine has been hampered by the apparent increased risk of agranuylocytosis. Based on clinical data, the incidence in patients treated for 52 weeks with clozapine is approximately 2%. Because of this risk, patients on a clozapine regimen have to be monitored continually for hematological signs of agranulocytosis onset. A simple screening procedure which reduced or eliminated the hematological monitoring required in clozapine therapy would be highly desirable in view of the considerable therapeutic potential of clozapine for patients who are unresponsive to or intolerant of the standard neuroleptic drugs.

DESCRIPTION OF THE PRIOR ART

J. A. Lieberman, et al., Arch. Gen. Psych., Vol. 47, pgs. 945-948 (1990) discloses a specific HLA phenotype in an Ashkenazi Jewish population as strongly associated with an increased risk of agranulocytosis, thereby giving rise to speculation that an immune mechanism may be responsible for drug-induced agranulocytosis. However, it is not clear that an identical HLA phenotype is present in non-Jewish patients affected with this disorder.

A. V. Pisciotta, et al., Ann. N.Y. Acad. Sci., Vol. 459, pgs. 198-210 (1985) discloses that clozapine is toxic to the granulocyte-macrophage hematopoietic stem cell [CFU-GM) and cultured fibroblasts at concentrations of 50 $\mu$M, a dose which is well above the therapeutic serum levels in patients.

DESCRIPTION OF THE INVENTION

It has now surprisingly been found that one of the major metabolites of clozapine, viz., N-desmethylclozapine, is much more toxic to normal bone marrow hematopoietic cells than either the parent compound clozapine or the other major metabolite of clozapine, viz., N-oxideclozapine. This discovery may be demonstrated by the following hematopoietic colony assay as follows:

Bone marrow was aspirated from the iliac crest of normal donors or donors with normal bone marrows who underwent an autologous bone marrow harvest, of which both groups of donors gave informed consent. Non-adherent mono-nuclear cells were isolated by allowing cells collected at the interface of a Ficoll-Hypaque gradient to adhere to Primaria tissue culture flasks (Falcon) as described by H. M. Lazarus, et. al. in Blood, Vol. 78, pgs. 830-837 (1991) and removing the non-adherent cells 2 hours later. These cells were then cultured at $1 \times 10^5$ cells/ml. in 0.8% methylcellulose in the presence of 200 units/ml GM-CSF, 50 units/ml IL-3, 2 units/ml erythropoietin, 100 $\mu$M hemin, 30% selected fetal calf serum, 1% deionized BSA and 100 $\mu$m alpha-thiothreitol in Iscove's modified Dulbecco medium (IDMD) as previously described in the H. M. Lazarus article mentioned above. The parent compound clozapine and its two major metabolites, viz., N-desmethylclozapine and N-oxideclozapine, were then added to the mixture in a concentration range of between 1 and 50 $\mu$g/ml. In one experiment, mononuclear cells which had not undergone adherence-depletion were suspended at $1 \times 10^6$ cells/ml in IDMD and incubated in the presence of clozapine and its two major metabolites for 24 hours, after which time the cells were washed free of the test compounds and then suspended in the methylcellulose culture for detection of colonies. Cell suspensions were then plated as 1 ml aliquots in 35 mm dishes (Nunc) and incubated at 37° C., 5% $CO_2$ in a humidified atmosphere for 14 days. CFU-GM (colony forming unit-granulocyte macrophage), BFU-E (burst forming unit-erythroid) and CFU-GEMM (multi-lineage cell) were identified using an inverted microscope and when necessary by histochemical stain as described by S. L. Gerson in Blood, Vol. 63, pgs. 878-885 (1984).

RESULTS

Employing the hematopoietic colony assay method described above, the following mean *IC$_{50}$'s were obtained:

| compound | CFU-GM | BFU-E | CFU-GEMM |
| --- | --- | --- | --- |
| clozapine | 14.6 $\mu$g/ml. | 12.0 $\mu$g/ml. | >10 $\mu$g/ml. |
| N-oxideclozapine | >50 $\mu$g/ml. | 11.8 $\mu$g/ml. | >10 $\mu$g/ml. |

-continued

| compound | CFU-GM | BFU-E | CFU-GEMM |
|---|---|---|---|
| N-desmethylclozapine | 2.5 µg/ml. | 3.2 µg/ml. | 2.4 µg/ml. |

*$IC_{50}$ - 50% of control cell count

In unaffected individuals receiving a standard daily dose of between 300 and 650 mg of clozapine, the range of steady state serum concentrations of clozapine is 0.1–0.8 µg/ml., the range for N-oxideclozapine is 0.05–0.3 µg/ml., and the range for N-desmethylclozapine is 0.1–0.8 µg/ml. Accordingly, from the above results, it can be concluded that whereas clozapine and N-oxideclozapine are toxic to all three stem cell lineages in the bone marrow only at concentrations above 10 µg/ml. (i.e., 10–50 times the normal serum levels achieved in unaffected individuals), N-desmethylclozapine is toxic to all three stem cell lineages at concentrations only a few times greater than those seen in unaffected individuals.

Based on the above results, coupled with the discovery that patients who develop clozapine-induced agranulocytosis have high serum concentrations of N-desmethylclozapine, as compared to those patients who do not develop agranulocytosis, the present invention accordingly provides a method of screening patients on clozapine therapy for vulnerability to developing agranulocytosis. Accordingly, in one aspect, the instant invention provides a method of detecting vulnerability to agranulocytosis complications in patients on clozapine therapy before the onset of agranulocytosis which comprises establishing the concentration of N-desmethylclozapine in the blood or bone marrow of said patients. Thus, a vulnerability level can be set in patients on clozapine therapy. For example, by employing a pre-set vulnerability level, viz., a serum concentration range of N-desmethylclozapine of between 1.0 and 2.0 µg/ml., preferably between 1.5 and 2.0 µg/ml., more preferably between 1.7 and 2.0 µg/ml., one can reliably predict a patient's vulnerability to agranulocytosis complications as the serum concentration of N-desmethylclozapine approaches the upper limit of the vulnerability level.

In another aspect, the instant invention provides a method of detecting the onset of agranulocytosis complications in patients on clozapine therapy which comprises establishing the concentration of N-desmethylclozapine in the blood or bone marrow of said patients. Thus, an onset level can be set in patients on clozapine therapy. For example, by employing a pre-set onset level, viz., a serum concentration of N-desmethylclozapine >2.0 µg/ml., preferably between 2.1 and 3.0 µg/ml., more preferably between 2.1 and 2.5 µg/ml., one can reliably predict the onset of agranulocytosis complications in a patient, i.e., if the serum concentration of N-desmethylclozapine exceeds 2.0 µg/ml., treatment on clozapine should be discontinued.

In a further aspect, the instant invention provides a method of determining patient sensitivity to N-desmethylclozapine comprising collecting peripheral blood from patients and testing it for sensitivity to N-desmethylclozapine in the stem cell assay. Thus, in a manner analogous to that described above, 10 ml of heparinized blood is collected and the growth of hematopoietic stem cells isolated from the whole blood is tested against N-desmethylclozapine and compared to a pre-set sensitivity level. For example, by employing the following $IC_{50}$ limits:

| stem cell lineage | $IC_{50}$ limit |
|---|---|
| CFU-GM | 1.0 µg/ml |
| BFU-E | 1.5 µg/ml |
| CFU-GEMM | 1.0 µg/ml | one can reliably predict a patient's sensitivity to N-desmethylclozapine as the $IC_{50}$ approaches the upper limit of the sensitivity level.

What is claimed is:

1. A method of detecting vulnerability to agranulocytosis complications in a patient on clozapine therapy before the onset of agranulocytosis which comprises establishing the concentration of N-desmethylclozapine in the blood serum or bone marrow of said patient, comparing the concentration of N-desmethylclozapine in the blood serum or bone marrow of said patient to a pre-set vulnerability level which is a concentration range of between 1.0 to 2.0 µg/ml of N-desmethylclozapine, and correlating the concentration of N-desmethylclozapine in the blood serum or bone marrow of said patient to a condition of vulnerability to agranulocytosis complications.

2. A method according to claim 1 wherein the concentration of N-desmethylclozapine is established in the blood serum of said patient.

3. A method according to claim 1 wherein the concentration of N-desmethylclozapine is established in the bone marrow of said patient.

4. A method according to claim 1 wherein the pre-set vulnerability level is a concentration range of N-desmethylclozapine of between 1.5 and 2.0 µg/ml.

5. A method according to claim 4 wherein the pre-set vulnerability level is a concentration range of N-desmethylclozapine of between 1.7 and 2.0 µg/ml.

6. A method of detecting the onset of agranulocytosis complications in a patient on clozapine therapy which comprises establishing the concentration of N-desmethylclozapine in the blood serum or bone marrow of said patient, comparing the concentration of N-desmethylclozapine in the blood serum or bone marrow of said patient to a pre-set onset level which is a concentration of >2.0 µg/ml of N-desmethylclozapine, and correlating the concentration of N-desmethylclozapine in the blood serum or bone marrow of said patient to the onset of agranulocytosis complications.

7. A method according to claim 6 wherein the concentration of N-desmethylclozapine is established in the blood serum of said patient.

8. A method according to claim 6 wherein the concentration of N-desmethylclozapine is established in the bone marrow of said patient.

9. A method according to claim 6 wherein the pre-set onset level is a concentration range of N-desmethylclozapine of between 2.1 and 3.0 µg/ml.

10. A method according to claim 9 wherein the pre-set onset level is a concentration range of N-desmethylclozapine of between 2.1 and 2.5 µg/ml.

11. A method of determining patient sensitivity to N-desmethylclozapine which comprises collecting heparinized blood from a patient, isolating CFU-GM, BFU-E and CFU-GEMM stem cells from said blood, subjecting said cells to a stem cell assay to determine the effect of N-desmethylclozapine on the growth of said cells, comparing the effect of N-desmethylclozapine on the growth of said cells to a pre-set sensitivity level which represents $IC_{50}$ limits for the respective stem cells, and correlating the effect of N-desmethylclozapine on the growth of said cells to a condition of sensitivity to N-desmethylclozapine.

13. A method according to claim 11 wherein the $IC_{50}$ limit for BFU-E is 1.5 µg/ml.

12. A method according to claim 11 wherein the $IC_{50}$ limit for CFU-GM is 1.0 µg/ml.

14. A method according to claim 11 wherein the $IC_{50}$ limit for CFU-GEMM is 1.0 µg/ml.

* * * * *